United States Patent [19]

Kötzsch et al.

[11] 3,985,781
[45] Oct. 12, 1976

[54] ESTERIFICATION METHOD FOR TRICHLOROSILANE

[75] Inventors: Hans Joachim Kötzsch, Rhinefelden; Hans Joachim Vahlensieck, Wehr, Baden, both of Germany

[73] Assignee: Dynamit Nobel Aktiengesellschaft, Troisdorf, Germany

[22] Filed: Feb. 27, 1975

[21] Appl. No.: 553,871

[30] Foreign Application Priority Data

Mar. 1, 1974 Germany............................ 2409731

[52] U.S. Cl........................................ 260/448.8 R
[51] Int. Cl.²........................ C07F 7/04; C07F 7/18
[58] Field of Search ............................ 260/448.8 R

[56] References Cited
UNITED STATES PATENTS

| | | | |
|---|---|---|---|
| 3,008,975 | 11/1961 | Schubert...................... | 260/448.8 R |
| 3,792,071 | 2/1974 | Nitzsche et al. ............. | 260/448.8 R |
| 3,806,549 | 4/1974 | Foley .......................... | 260/448.8 R |

*Primary Examiner*—Paul F. Shaver
*Attorney, Agent, or Firm*—Burgess, Dinklage & Sprung

[57] ABSTRACT

A process for the preparation of a partial or complete trichlorosilane ester of the formula

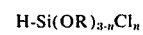

$$H\text{-}Si(OR)_{3-n}Cl_n$$

wherein $n$ is 0 or 1, R is an alkyl group of 1 to 11 carbon atoms, an alkyl group of 1 to 11 carbon atoms containing an oxygen atom in the chain, or an alkyl group of 1 to 11 carbon atoms containing a sulfur atom in the chain which comprises:

1. Forming a partial esterification product by contacting a trichlorosilane with up to a 10% stoichiometric excess of a primary alcohol, the stoichiometric amount corresponding to only partial esterification of said trichlorosilane, said contacting being conducted only in the liquid phase without any contact in the vapor phase;

2. Removing HCl formed from the reaction vessel;

3. Thereafter contacting the partial esterification product with additional primary alcohol and removing liberated residual HCl from the reaction vessel.

15 Claims, No Drawings

ESTERIFICATION METHOD FOR TRICHLOROSILANE

BACKGROUND OF THE INVENTION

1. Field of the Invention

This invention relates to the preparation of complete or partial esterification products of trichlorosilane by a direct process involving the reaction of a primary alcohol with trichlorosilane whereby there is obtained a complete or partial ester having the formula $$H\text{-}Si(OR)_{3-n}Cl_n$$

wherein R represents an alkyl radical of 1 to 11 carbon atoms which can contain heteroatoms such as oxygen or sulfur in the chain and $n$ is equal to 0 or 1. This invention is particularly concerned with the recovery of such partial or complete esterification products in high yields, especially in excess of 90%, based upon the amount of trichlorosilane employed.

DISCUSSION OF THE PRIOR ART

Several procedures are already known which are designed for the esterification of trichlorosilane utilizing alcohols. Several authors have described the reaction of trichlorosilane with stoichiometric quantities of an alcohol, especially ethanol. The variations in the procedures essentially involve the nature and quantity of any solvent and the reaction temperatures. Unfortunately, in all of the esterifications performed by a batch method, appreciable and usually absolutely predominant secondary reactions prevail. These reactions prevail to such an extent that the methods are considered impractical for the preparation of these compounds, impractical in the sense that poor yields of the desired esterification product are provided.

Large amounts of hydrogen chloride are formed during such process which not only cleaves the alkoxysilane group back to the alkanol and the chlorosilane but also splits the hydrogen-silane bond whereby to yield hydrogen and to form an alkoxy-silane bond and a chlorosilane bond. In this manner, the desired hydrogen-silane ester is usually completely lost. Additionally, the hydrogen chloride forms chloroalkanes with the alkanols and water as an intermediate product. This in turn attacks the chlorosilane and the alkoxysilanes by effecting a hydrolysis.

Researchers have turned to the continuous process to diminish the danger resulting from the presence of HCl product. In fact, the continuous process does diminish the danger of the complete destruction of the product by the named secondary reactions which are quite prevalent in batch processes. The continuous process does this by exploiting the opportunity of maintaining the reaction time as short as possible. However, products have been encountered in the raw products as described above and the continuous process does not solve these problems. Hence, in a continuous process continuous separation of the hydrogen chloride formed would be required, and such separation would have to effect separation of the HCl in large quantities. In the continuous esterification of trichlorosilane, one disadvantage resides in that rather expensive apparatus is required. The continuous process described in French Pat. No. 1,316,295 illustrates that the above-described disadvantages cannot be eliminated, and that it is mostly the tetraalkoxysilanes that are formed as the end product.

Attempts have been made to form hydrogen-containing alkoxysilanes by the reaction of metallic silicon with alcohols. In this process, however, there is almost exclusively formed the tetraalkoxysilanes owing to the presence in the metallic silicon of metals such as iron, zinc and copper. These metals have a strong catalytic action on all intermediately forming hydrogen alkoxysilanes and there results a disproportionation favoring the formation of tetraalkoxysilane and monosilane. On account of the hazardous monosilane occurring in residual amounts together with the escaping hydrogen, the process entails considerable risk.

It has therefore become desirable to provide a direct process for the preparation of hydrogen-containing alkoxysilanes, particularly di- and trialkoxysilanes, which process utilizes reactants which give no rise to risk. It has become particularly desirable to provide a process which can be carried out to provide high yields of the desired hydrogen-containing alkoxysilane, preferably a process which utilizes as a reactant trichlorosilane. More especially, it has become desirable to provide an improved batch process for the preparation of hydrogen-containing alkoxysilanes wherein the alkoxysilane is obtained in a yield in excess of 90%, based upon the amount of trichlorosilane employed.

SUMMARY OF THE INVENTION

The long-felt desires of the art are fulfilled in accordance with the present invention which provides a process for the preparation of a trichlorosilane ester of the formula $$H\text{-}Si(OR)_{3-n}Cl_n$$

wherein $n$ is 0 or 1, R is an alkyl group of 1 to 11 carbon atoms, an alkyl group of 1 to 11 carbon atoms containing an oxygen atom in the chain or an alkyl group of 1 to 11 carbon atoms containing a sulfur atom in the chain, which process comprises:

1. Forming a partial esterification product by contacting trichlorosilane with up to a 10% stoichiometric excess of a primary alcohol, the stoichiometric amount corresponding to only partial esterification of said trichlorosilane, said contacting being conducted only in the liquid phase and without contact in the vapor phase;
2. Removing HCl formed from the reaction vessel;
3. Thereafter, contacting the partial esterification product with additional primary alcohol and removing liberated residual HCl from the reaction vessel.

The difficulties experienced in the prior art processes are reliably eliminated, in accordance with the present invention, whereby in a first step a maximum of two of the available valences of the trichlorosilane are esterified, i.e., an intermediate chloroalkoxysilane product is prepared. This intermediate product is prepared by reacting substantially a stoichiometric amount of a primary alcohol with trichlorosilane, the primary alcohol contacting the trichlorosilane only in the liquid phase and without contact in the vapor phase. This is performed by introducing the primary alcohol into the trichlorosilane in the liquid phase as by use of a tube submerged below the liquid level of the trichlorosilane. At the termination of the first partial esterification, the HCl formed during such process is removed. One method for removal is to heat the reaction mixture to boiling to drive off any residual HCl therein. The esterification can then be completed by the addition of further primary alcohol according to the degree of esterification desired.

It must be realized that the present process can be performed to prepare as a final product di- or trialkoxysilane. In other words, the final product can itself be only a partial ester of trichlorosilane. Generally speaking, the process is carried out with a view to preparing a completely esterified trichlorosilane. In any event, the method of the invention operates on the basis of the following equations:

1. 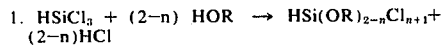
   $(2-n)HCl$

2. 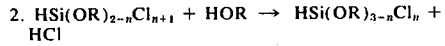
   $HCl$

DESCRIPTION OF PREFERRED EMBODIMENTS

Referring to the reactions above, the first step, represented by reaction 1, is preferably performed at temperatures below 100° C, more preferably at temperatures below 90° C. Since the reaction is endothermic, no particular steps are required to perfect cooling. The reaction can be performed at the temperature which establishes itself in the reaction chamber. As soon as the reaction of reaction 1 is complete, but before three hours have elapsed, the hydrogen chloride is removed from the reaction mixture and from the the reaction chamber. This is accomplished preferably by driving it off by the use of heat.

The esterification reactions of steps 1 or 3 can be accomplished without the use of a solvent. However, a solvent can also be employed. The use of a solvent depends, among other things, on the nature of the primary alkanol being employed. When higher alkanols are used, the use of a solvent is desirable.

After the removal of hydrogen chloride, the amount of alcohol that is stoichiometrically required in order to produce the desired degree of esterification is introduced to the reaction mixture. It is unnecessary to maintain the temperature during the final esterification within any temperature limit. However, the addition of additional alkanol should not be extended over a period greater than three hours. Following the final esterification, any additional hydrogen chloride that may have been released is again removed, for instance by heating the reaction mixture at ebullition or boiling.

In both of the periods during which the primary alcohol is added, it is preferably fed through a tube which feeds the alcohol directly into the liquid phase without allowing it to come in contact with the trichlorosilane and hydrogen chloride in the vapor phase, i.e., in the vapor phase above the liquid phase within the reaction vessel.

Following termination of the reaction the raw products can be refined in the usual way without delay and by known methods, preferably by distillation.

Referring to reaction 1, it is not critical that a precise stoichiometric amount of alcohol be introduced, for even a slight excess of alcohol, up to a stoichiometric excess of about 10%, can be employed. This also applies to the final esterification. Even if there is a slight excess of alcohol, the reaction takes place in accordance with the equations set forth above to provide high yields of the desired product.

Surprisingly, when the method of the present invention is employed, the above-described secondary reactions hardly occur. The desired hydrogen silane alkyl esters are produced in yields of more than 90% with respect to the trichlorosilane input. In view of the known difficulties which mitigate against high ester yield, this outcome could hardly have been anticipated.

The reaction apparatus normally employed consists preferably of a glass or enameled stirrer vessel with a receiver for trichlorosilane and alkanol, the latter having a glass or Teflon delivery tube immersed in the liquid phase in the stirrer vessel. A large reflux condenser is attached to the apparatus which operates at temperatures between −40° and −80° C. The purpose of this reflux condenser is to refrigerate the hydrogen chloride occurring as by-product in the reaction vessel which is driven off during the HCl removal. This HCl so removed can be discharged from the condenser into a recirculating liquid hydrochloric acid solution, or it can be introduced directly into milk of lime where it is neutralized. Other methods for the safe absorption and removal of HCl would be apparent to one of skill in the art.

Numerous alkanols, particularly primary alkanols, can be used in accordance with the present invention. Those preferred reactants for addition to the trichlorosilane include methanol, ethanol, propanol, butanol, 2-methoxyethanol, diethyleneglycol monomethyl ether and ethylene glycol monoacetate.

Suitable solvents are those which do not dissolve hydrogen halide or its salts, examples being chlorinated hydrocarbons such as trans- or cis-dichloroethylene, trichoroethylene, perchloroethylene, and liquid hydrocarbons having boiling points up to 150° C such as the various benzine fractions or aromatic hydrocarbons such as benzene.

For the refinement of the raw product, distillation through a column containing four to six trays suffices as a rule, in vacuo if desired. In this manner pure hydrogen trialkoxysilanes with acidities of less than 20 ppm can easily be obtained. From the column residues the valuable accompanying substances, tetramethoxysilane, tetraethoxysilane, tetra-2-methoxyethoxysilane, etc., are isolated in small amounts.

By these methods of the invention, trimethoxysilane, triethyoxysilane, tripropoxysilane, tributoxysilane and tris-2-methoxyethoxysilane, for example, can be prepared with good yields. Compounds of this class have an increasing technical importance for the synthesis of organofunctional silane compounds and in semiconductor chemistry.

In order to more fully illustrate the nature of the invention and the manner of practicing the same, the following examples are presented.

EXAMPLE 1

Esterification of trichlorosilane with methanol to trimethoxysilane 5400 g (40 moles) of trichlorosilane were placed in a ten-liter multiple-necked flask equipped with an internal thermometer, a nitrogen gas-shielded reflux condenser (−80° C) with a discharge line runnning to a receiver charged with milk of lime, a dropping funnel with a drain tube discharging below the liquid level, a paddle stirrer, a heating coil and cooling coil in the reaction chamber, and a 25 mm bottom drain valve. Without any input of heat, 2560 g (80 moles) of anhydrous methanol were fed over a period of 95 minutes, with stirring, through the submerged supply tube, whereupon an internal temperature of −11° C established itself. Then the mixture was heated with stirring, over a period of about 20 minutes, to ebullition at about 69° C. The heating was shut off after this temperature was reached, and immediately an additional 1280 g (40 moles) of methanol was fed in through the submerged tube over a period of 20 minutes, with stirring, whereupon an internal temperature of 64° C established itself. After the addition of the methanol was completed, the mixture was heated again over a period of 45 minutes to ebullition at 84.5° C, and then cooked-out, still boiling raw product was drained into the bottom of a six-tray column containing 4 mm porcelain saddles as packing, for immediate distillation.

The gas-chromatographic analysis of the raw product showed a content of 92.6% trimethoxysilane plus 6.2% tetramethoxysilane and about 1% dimethoxychlorosilane.

Fractional distillation yielded 4430 g (90.6%) trimethoxysilane, boiling point 84° C; $D_4^{20} = 0.9589$.

EXAMPLE 2

Esterification of trichlorosilane with 2-methoxy-ethanol to tris-2-methoxyethoxysilane In the same manner as in Example 1, 1900 g (14 moles) of trichlorosilane mixed with 1820 g of trans-1,2-dichloroethylene were placed in the flask and over a period of 20 minutes 2130 g (28 moles) of anhydrous methyl glycol were fed through the submerged tube, whereupon an internal temperature of +14° C established itself. Then, over a period of 50 minutes, the mixture was heated with stirring to approximately 72° C, and over a period of 10 minutes 1065 g (14 moles) of additional methyl glycol were fed in through the tube, an internal temperature of about 67° C establishing itself. After this addition was completed the mixture was again heated over a period of about 30 minutes to ebullition at 82° C, and the cooked-out, still boiling raw product was transferred to the still where it was freed of the solvent, finally at 30 Torr, and at a temperature of 120° C at the bottom of the distillation column. The hot product was drained into the bottom of a five-to six-tray column of 65 mm diameter packed with monel multifil for further refinement in vacuo.

Gas chromatographic analysis of the raw product showed a content of 90.8% tris-2-methoxyethoxysilane and 5.6% tetra-2-methoxyethoxysilane.

The fractional distillation yielded 3200 g (90.0%) tris-2-methoxyethoxysilane, boiling point 103° C (1 Torr), $D_4^{20} = 1.0545$, $n_D^{20} = 1.4162$, flame point 118° C.

The active hydrogen amounted to 90 Nml/g (calculated: 89 Nml/g).

Elemental analysis ($C_9H_{22}O_6Si$, molecular weight 254)

|            | C     | H    | Si    |
|------------|-------|------|-------|
| Calculated | 42.5% | 8.7% | 11.0% |
| Found      | 42.7% | 8.9% | 10.8% |

Comparative Experiment 1 - Esterification of trichlorosilane with ethanol without the submerged tube, in a single reaction stage.

1355 g (10 moles) of trichlorosilane were placed in a four-liter multiple-necked flask equipped with internal thermometer, a nitrogen-shielded reflux condenser (−80° C) with exhaust gas line running to a receiver charged with milk of lime, a normal dropping funnel with its bottom extending into the gas phase of the flask, a paddle stirrer, a heating coil and a cooling coil in the reaction chamber, and a 25 mm bottom drain valve. Over a period of 80 minutes 1380 g (30 moles) of anhydrous ethanol were fed in, with stirring, without heat input, whereupon an internal temperature of 29° C established itself. After the addition of the ethanol was completed the mixture was heated over a period of 40 minutes to ebullition at 149° C, and the cooked, still boiling raw product was transferred to the still.

Gas chromatographic anaysis of the raw product showed a content of about 11% of a mixture of triethoxysilane and diethoxychlorosilane plus about 79% chlorotriethoxysilane and less than 10% tetraethoxysilane. Fractionation yielded 152 g (about 10%) of a mixture of triethoxysilane and chlordiethoxysilane (active hydrogen: 142 Nml/g) in the boiling range between 119° and 134° C, and 1522 g (about 77%) of chlortriethoxysilane of a boiling point of 154° to 158° C.

Comparative Experiment 2 - Esterification of trichlorosilane with ethanol using a submerged tube, in a single reaction state.

The experimental apparatus of Comparative Experiment 1 was equipped with a dropping funnel whose outlet was submerged in the reaction liquid in accordance with the invention. Then the procedure of Comparative Experiment 1 was followed, whereupon an internal temperature of +14° C established itself.

Processing yielded a crude product containing 52% triethoxysilane, which was also recovered by distillation.

Comparative Experiment 3 - Esterification of trichlorosilane with ethanol using a submerged tube, in a single reaction stage at low temperature.

The procedure was similar to Comparative Experiment 2, but the two reaction components were chilled to −43° C before beginning, and the entire course of the reaction was controlled by thermostat at an internal temperature of −43° C. When the addition of ethanol was completed the hydrogen chloride was largely removed in vacuo over a period of 40 minutes while the internal temperature was maintained at −43° C, and the raw product was delivered for distillation. Immediate distillation brought a yield of 47% triethoxysilane.

EXAMPLE 3

Esterification of trichlorosilane with ethanol to triethoxysilane (pursuant to the invention)

In the manner described in Example 1, 2710 g (20 moles) of trichlorosilane were placed in the flask and over a period of 40 minutes 1840 g (40 moles) of anhydrous ethanol were delivered through the submerged tube, whereupon an internal temperature of −1° C established itself. Then, over a period of about 20 minutes, the temperature was raised, with stirring, to about 113° C and 920 g (20 moles) of additional ethanol was fed through the submerged tube over a period of 15 minutes, an internal temperature of 93° C establishing itself. Upon completion of the addition of ethanol the flask was again heated to ebullition at 132.5° C and the cooked, still boiling raw product was transferred to the bottom of the still.

Gas chromatographic analysis of the raw product showed a content of 94.1% triethoxysilane plus about 4.7% tetraethoxysilane. Fractional distillation yielded 3030 g (92.5%) triethoxysilane having a boiling point at 132° C; $D_4^{20} = 0.8771$.

What is claimed is:

1. A process for the preparation of a trichlorosilane ester of the formula

wherein $n = 0$ or 1, R is an alkyl group of 1 to 11 carbon atoms, an alkyl group of 1 to 11 carbon atoms containing an oxygen atom in the chain or an alkyl group of 1 to 11 carbon atoms containing a sulfur atom in the chain which comprises
   1. forming a partial esterification product by contacting trichlorosilane with up to a 10% stoichiometric excess of a primary alcohol, the stoichiometric amount corresponding to only partial esterification of said trichlorosilane, said contacting being conducted only in the liquid phase and without contact in the vapor phase;
   2. removing HCl formed from the reaction vessel;
   3. thereafter contacting the partial esterification product with additional primary alcohol and removing liberated residual HCl from the reaction vessel.

2. A process according to claim 1 wherein the reactants in steps 1 and 3 are maintained at a temperature below 100° C.

3. A process according to claim 1 wherein th primary alcohol is contacted with the trichlorosilane or partial esterification product thereof by passing it through a tube submerged beneath the liquid level of said trichlorosilane or partial esterification product thereof.

4. A process according to claim 1 wherein said primary alcohol is selected from the group consisting of methanol, ethanol, propanol, butanol, 2-methoxyethanol, diethyleneglycol monomethyl ether and ethylene glycol monoacetate.

5. A process according to claim 1 wherein step 1 is carried out in the presence of a solvent.

6. A process according to claim 5 wherein the solvent consists essentially of a chlorinated hydrocarbon.

7. A process according to claim 6 wherein said chlorinated hydrocarbon is selected from the group consisting of trans-dichloroethylene, cis-dichloroethylene, trichloroethylene and perchloroethylene.

8. A process according to claim 5 wherein said solvent consists essentially of a liquid hydrocarbon having a boiling point up to 150° C.

9. A process according to claim 1 wherein HCl is removed from the reaction vessel within three hours of the completion of esterification.

10. A process according to claim 1 wherein the HCl is removed by heating the reaction mixture to boiling.

11. A process according to claim 1 wherein step 1 is carried out in the absence of a solvent.

12. A process according to claim 1 wherein step 3 is carried out in the absence of a solvent.

13. A process according to claim 1 wherein steps 1 and 3 are carried out in the absence of a solvent.

14. A process according to claim 5 wherein said solvent consists essentially of a benzine fraction.

15. A process according to claim 5 wherein said solvent consists essentially of benzene.

* * * * *